United States Patent [19]

Schmidt

[11] 4,374,286
[45] Feb. 15, 1983

[54] HYDRATION OF OLEFINS

[75] Inventor: Robert J. Schmidt, Rolling Meadows, Ill.

[73] Assignee: UOP Inc., Des Plaines, Ill.

[21] Appl. No.: 352,839

[22] Filed: Feb. 26, 1982

[51] Int. Cl.$^3$ .............. C07C 29/10; C07C 29/04; C07C 27/02

[52] U.S. Cl. .............. 568/907; 568/671; 568/877

[58] Field of Search .............. 568/907, 877

[56] References Cited

U.S. PATENT DOCUMENTS

| | | | |
|---|---|---|---|
| 2,045,785 | 6/1936 | Lewis | 568/907 |
| 2,317,949 | 4/1943 | Burk | 568/877 |
| 2,373,359 | 4/1945 | Voogd et al. | 568/886 |
| 2,519,061 | 8/1950 | Mason | 568/907 |
| 2,533,808 | 12/1950 | Howlett et al. | 568/889 |
| 2,974,175 | 3/1961 | Watts et al. | 568/907 |
| 3,095,458 | 6/1963 | Judice et al. | 568/890 |

Primary Examiner—Joseph E. Evans
Attorney, Agent, or Firm—James R. Hoatson, Jr.; Raymond H. Nelson; William H. Page, II

[57] ABSTRACT

Alcohols may be obtained by an indirect hydration of olefinic hydrocarbons in which the olefinic hydrocarbon is first esterified by treatment with an inorganic acid to form dialkyl and alkyl hydrogen salts. These salts are then trans-esterified by treatment with an organic acid to form an organic ester. The reconstituted inorganic acid is separated from this mixture by stripping and recycled, while the organic esters are then treated with water in a hydrolysis step to reconstitute the organic acid and form the desired alcohol and ether. The alcohol product is separated from the ether which may then be further treated by thermal decomposition or hydrolysis to form an additional amount of the desired alcohol.

19 Claims, 1 Drawing Figure

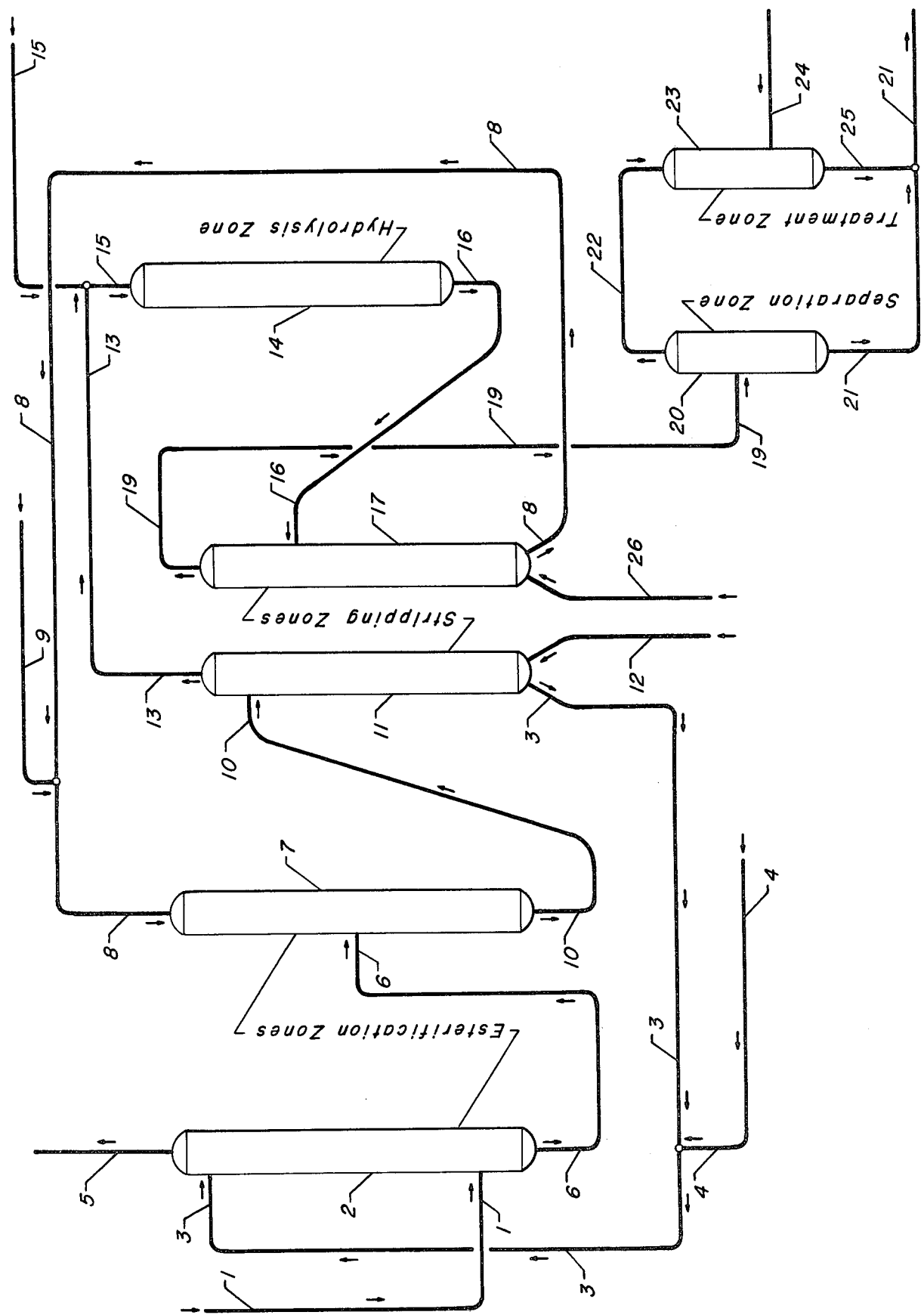

HYDRATION OF OLEFINS

BACKGROUND OF THE INVENTION

The indirect hydration of olefins to alcohols and ethers has employed, in the conventional process, sulfuric acid as the esterification agent to form dialkyl sulfate and alkyl hydrogen sulfate esters. However, in the conventional processes, it is necessary to effect a costly reconcentration or reconstitution of sulfuric acid, the reconcentration resulting from the hydrolysis of the esters with an excess of water in order to prepare the necessary alcohols. The use of alcohols in the chemical industry is well known and covers a wide variety of fields. For example, ethyl alcohol is a staple alcohol of commerce and is used as a solvent, as an intermediate in organic derivatives of dyes, synthetic rugs, synthetic rubber, detergents, surface coatings, cosmetics, pharmaceuticals, explosives, beverages, etc. Likewise, propyl alcohol and especially isopropyl alcohol is used in the manufacture of acetone, as a solvent for essential and other oils, gums, resins, etc., deicing agent for liquid fuels, pharmaceuticals, perfumes, lacquers, etc., while butyl alcohol is used as a solvent in varnish, lacquers, etc. In addition, other alcohols may be used as a component in fuels such as gasoline, etc.

As will hereinafter be shown in greater detail, it has now been discovered that an olefinic hydrocarbon may be hydrated to form an alcohol as well as an ether by utilizing an inorganic acid as a first esterification agent followed by the use of an organic acid as a trans-esterification agent, thereby eliminating the requirement of reconcentrating the acids which are utilized as the aforesaid esterification agents.

SUMMARY OF THE INVENTION

This invention relates to a process for the indirect hydration of an olefinic hydrocarbon to an alcohol and ether. More specifically, the invention is concerned with a process for the indirect hydration of an olefinic hydrocarbon to an alcohol and ether utilizing a concentrated inorganic acid as the primary esterification agent and an organic acid as a trans-esterification agent.

As will be shown in greater detail, by utilizing the process conditions and flow scheme of the present process, it has now been discovered that an indirect hydration of an olefinic hydrocarbon to form a desired product may be accomplished in a commercially attractive and economical manner, thus obviating the need for relatively costly equipment and process modification.

It is therefore an object of this invention to provide a process for the indirect hydration of an olefinic hydrocarbon while avoiding the addition of an excess amount of hydrating agent.

A further object of this invention is to provide a process for obtaining alcohols from olefinic hydrocarbons while avoiding the necessity for reconcentrating the esterification agent utilized in said process.

In one aspect, an embodiment of this invention is found in a process for the hydration of an olefinic hydrocarbon which comprises esterifying said olefinic hydrocarbon with an inorganic acid at esterification conditions in a first esterification zone, subjecting the resultant alkyl salts to trans-esterification by treatment with an inorganic acid at esterification conditions in a second esterification zone, stripping the reconstituted inorganic acid from the resultant organic ester, hydrolyzing said organic ester with water at hydration conditions in a hydration zone, stripping the reconstituted organic acid from the resultant alcohol and ether hydrolysis product, separating and recovering said alcohol from said ether at separation conditions in a separation zone, treating said ether at treatment conditions in a treatment zone to produce an additional amount of said alcohol, and recovering said alcohol.

A specific embodiment of this invention is found in a process for the hydration of ethylene which comprises esterifying said ethylene with concentrated sulfuric acid at a temperature in the range of from about 50° to about 150° C. and a pressure in the range of from about 200 to about 1500 psi, subjecting the resultant diethyl sulfate and ethyl hydrogen sulfate to trans-esterification by treatment with acetic acid at a temperature in the range of from about 50° to about 150° C. and a pressure in the range of from about 200 to about 1500 psi, stripping the resultant ethyl acetate from the reconstituted sulfuric acid by treatment with nitrogen at a temperature in the range of from about ambient to about 200° C. and a pressure in the range of from about atmospheric to about 1500 psi, hydrolyzing said ethyl acetate by treatment with water at a temperature in the range of from about ambient to about 200° C. and a pressure in the range of from about atmospheric to about 1500 psi, stripping the resultant ethyl alcohol and diethyl ether from the reconstituted acetic acid utilizing a stripping gas comprised of nitrogen at a temperature in the range of from about ambient to about 200° C. and a pressure in the range of from about atmospheric to about 1500 psi, separating said ethyl alcohol and said diethyl ether at a temperature in the range of from about ambient to about 200° C. and a pressure of from about subatmospheric to about 150 psi and recovering said ethyl alcohol, treating said diethyl ether by hydrolysis with water at a temperature in the range of from about 150° to about 250° C. and a pressure in the range of from about subatmospheric to about 1500 psi to produce an additional amount of ethyl alcohol and recovering the desired ethyl alcohol.

Other objects and embodiments will be found in the following further detailed description of the present invention.

DESCRIPTION OF THE INVENTION

As hereinbefore set forth, the present invention is concerned with a process for the indirect hydration of olefinic hydrocarbons to form the corresponding alcohol and ethers utilizing a process which includes a first esterification step in which the esterification agent comprises an inorganic acid, and particularly a concentrated inorganic acid, followed by trans-esterification of the resulting alkyl salts with an organic acid. By utilizing the process of this invention, it is possible to avoid the dilution of the acids which are employed as the esterification agents while achieving a substantially 100% conversion of the organic acid. The achievement resulting in the use of an organic acid in the second esterification zone instead of H₂O will eliminate the need for a reconcentration of the acids employed, thus requiring only a reconstitution of the acids which may be recycled to the first and second esterification zones for further use as the desired agent with the concomitant elimination of added equipment, expenditure of energy and reduction in cost.

The process described herein involves the utilization of a dilute olefinic hydrocarbon feedstock such as offgases resulting from a prior refining or reforming operation. The olefins may be present as a mixture of gases containing from 2 to about 4 carbon atoms or more in the chain, specific examples of these olefinic hydrocarbons being ethylene, propylene, butylene, etc. It is also contemplated within the scope of this invention that olefinic hydrocarbons containing more than 4 carbon atoms such as the isomeric amylenes, hexenes, heptenes, octenes, nonenes, decenes, etc. may also be utilized as feedstocks for the preparation of alcohols and ethers.

Examples of inorganic acids which may be employed to effect the first esterification step of the present process, preferably in a concentrated state, will include sulfuric acid, sulfurous acid, phosphoric acids such as orthophosphoric acid, pyrophosphoric acid, etc., phosphorous acid, hydrochloric acid, hydrobromic acid, hydroiodic acid, hydrofluoric acid, chlorosulfonic acid, bromosulfonic acid, nitrous acid, boric acid, carbonic acid, iodic acid, the heteropoly acids of tungsten, molybdenum and vanadium such as tungstophosphoric acid, tungstosilicic acid, molybdophosphoric acid, molybdosilicic acid, vanadophosphoric acid, etc.

As an example of the process, when utilizing sulfuric acid as the first esterification agent, the feedstock is charged to an esterification zone wherein it is contacted with the esterification agent such as concentrated sulfuric acid, said acid being present in an amount in the range of from about 30% to 97% by weight of the acid solution. The first esterification zone is maintained by esterification conditions which will include a temperature in the range of from about 50° to about 150° C. and a pressure in the range of from about 200 to about 1500 psi. After allowing the first esterification process to proceed for a predetermined period of time, the resulting dialkyl sulfate and alkyl hydrogen sulfate esters are withdrawn from the esterification zone and passed to a second esterification zone. Any unreacted gases may be vented from the esterification zone for utilization as fuel, etc.

In the second esterification zone, the dialkyl and alkyl hydrogen esters or salts are subjected to a trans-esterification reaction by contact with an organic acid. Some specific examples of organic acids which may be employed in this second esterification zone will include fatty acids, preferably of relatively low molecular weight such as formic acid, acetic acid, propionic acid, butyric acid, chloro-substituted fatty acids such as chloroacetic acid, bromoacetic acid, trichloroacetic acid, chloropropionic acid, bromopropionic acid, chlorobutyric acid, bromobutyric acid, etc. It is to be understood that these acids are merely representative of the class of organic acids which may be employed to effect the trans-esterification reaction, and that the present invention is not necessarily limited thereto. As in the first esterification zone, the esterification conditions which are employed to effect the desired reaction will include a temperature in the range of from about 50° to about 150° C. and a pressure in the range of from about 200 to about 1500 psi. After allowing the trans-esterification process to proceed for a predetermined period of time, the resultant organic esters, reconstituted inorganic acids as well as any unreacted alkyl salts are withdrawn from the trans-esterification zone and passed to a stripping zone or column wherein the mixture is contacted with a stripping agent such as nitrogen, at stripping conditions which include a temperature in the range of from about ambient to about 200° C. and a pressure in the range of from about atmospheric to about 1500 psi, whereby the reconstituted inorganic acid and unreacted alkyl salts are separated from the organic ester and recycled back to the first esterification zone. The organic esters are then passed to a hydrolysis zone.

In the hydrolysis zone which is maintained at hydrolysis conditions including a temperature range of from ambient (20°–25° C.) up to about 200° C. or more and a pressure ranging from atmospheric to about 1500 psi, the organic esters are converted to the corresponding alcohols and ethers by treatment with water, while the organic acid is reconstituted. The mixture of alcohols and ethers and reconstituted acids is then withdrawn from this hydrolysis zone and passed to a second stripping zone wherein the mixture is contacted with a stripping agent such as nitrogen utilizing stripping conditions similar in nature to those hereinbefore set forth with regard to the first stripping zone.

The stripped alcohols and ethers are withdrawn from this stripping zone and passed to a separation zone, while the reconstituted organic acid is recycled back to the second esterification or trans-esterification zone.

In the separation zone, the alcohols and ethers are separated by conventional means such as distillation, while employing separation conditions which again will include temperatures in the range of from about ambient to about 200° C. utilizing pressures which may range from about subatmospheric (1 psia) to about 150 psi. The alcohol which is separated from the ether is recovered while the latter may then be further treated in a treating zone whereby the ether is converted to the desired alcohol and olefinic hydrocarbon, the latter being recycled to the first esterification zone. The treatment of the ether to form the desired alcohol may be effected in either a thermal manner or by hydrolysis. The thermal treatment of the ether to form the alcohol will be effected at treating conditions which will include a temperature in the range of from about 500° to about 750° C. while employing a pressure in the range of from about subatmospheric to about 1500 psi. It is contemplated that the thermal decomposition of the ether to the alcohol and olefinic hydrocarbon may be effected in the presence of an acidic type catalyst which will include such compounds as acidic resins; high surface area inorganic oxides such as alumina, silica-alumina, etc.; zeolites; etc. When utilizing a hydrolysis treatment to form the desired alcohol, the ether will be treated with water at a temperature in the range of from about 150° to about 250° C. utilizing pressures similar to those hereinbefore set forth, that is, from about subatmospheric to about 1500 psi. The olefinic hydrocarbons which are obtained by the decomposition of the ether may then be used as feeds for other processes or, if so desired, may be recycled back to the esterification zone for further treatment with a concentrated sulfuric acid to form the aforementioned sulfate esters.

BRIEF DESCRIPTION OF THE DRAWING

The present process will be further illustrated with reference to the accompanying FIGURE which illustrates a simplified flow diagram of the inventive feature of the present process. Various valves, coolers, condensers, pumps, heaters, controllers, etc. have been eliminated as not being essential to the complte understanding of the present invention. However, the illustration of these, as well as other essential appurtenances will become obvious as the drawing is described.

Referring now to the FIGURE, a feedstock such as an off-gas obtained from a reforming operation containing dilute olefinic hydrocarbons or a feedstock containing pure olefinic hydrocarbons is charged through line 1 to a first esterification zone 2. In first esterification zone 2, the feedstock is contacted with an inorganic acid of the type hereinbefore set forth which is charged through line 3 to zone 2. The amount of inorganic acid which is used to effect the esterification of the olefinic hydrocarbon is predetermined and may require the addition of some make-up acid which is charged through lines 4 and 3 to zone 2. In the first esterification zone 2, dialkyl salts, and in the event a dibasic acid is employed, alkyl hydrogen salts are formed. Any feed gas which remains from the esterification reaction is discharged from zone 2 through line 5 and may, if so desired, be used as fuel to form liquid petroleum gas, etc. The dialkyl salt and alkyl hydrogen salt esters which are formed in first esterification zone 2 are withdrawn therefrom through line 6 and passed into a second esterification zone 7. In esterification zone 7, the salts are contacted with an organic acid also of the type hereinbefore set forth which is charged to second esterification zone 7 through line 8. In addition, any make-up organic acid which may be required is also charged to esterification zone 7 through lines 9 and 8. In the second esterification zone, a trans-esterification reaction is effected whereby an organic ester is formed and the inorganic acid is reconstituted.

The reaction mixture comprising the organic ester, reconstituted inorganic acid and any unreacted alkyl salts are withdrawn from esterification zone 7 through line 10 and charged to stripping zone 11. In stripping zone 11, the mixture is contacted with a stripping agent such as nitrogen which is charged to zone 11 through line 12. In stripping zone 11, the reconstituted inorganic acid and the unreacted alkyl salts are stripped from the organic ester and recycled back to esterification zone 2 through line 3.

The organic ester which was formed in esterification zone 7 and which was stripped from the reconstituted inorganic acid in zone 11 is withdrawn from stripping zone 11 through line 13 and passed to hydrolysis zone 14. In hydrolysis zone 14, which is maintained at hydrolysis conditions which include a temperature in the range of from about ambient to about 200° C. and a pressure ranging from atmospheric to about 1500 psi, the organic ester is contacted with a stoichiometric amount of water which is added to zone 14 through line 15. The reaction mixture comprising the reconstituted organic acid and the hydrolysis product comprising a mixture of alcohol and ether is withdrawn from hydrolysis zone 14 through line 16 and passed to a second stripping zone 17. In stripping zone 17, the reaction mixture is subjected to the action of a stripping agent which, again, may comprise nitrogen added through line 26, whereby the reconstituted organic acid is withdrawn through line 8 and recycled back to second esterification zone 7. The hydrolysis product comprising a mixture of alcohol and ether is withdrawn from the second stripping zone 17 through line 19 and passed to separation zone 20.

In separation zone 20, which is maintained at a temperature in the range of from about ambient to about 200° C. and a pressure which may range from subatmospheric (1 psia) up to about 150 psi, the desired alcohol product is separated from the dialkyl ether and withdrawn from separation zone 20 through line 21 where it is passed to storage. The dialkyl ether which is separated from the alcohol is withdrawn from separation zone 20 through line 22 and passed to treatment zone 23.

In treating zone 23, the dialkyl ether may be treated in either a thermal decomposition manner at temperatures which may range from about 500° C. up to about 750° C. to form the corresponding alcohol and olefinic hydrocarbon, or, alternatively, the ether may be subjected to hydrolysis by treatment with water which, in the event that such a treating system is used, will be charged to treatment zone 23 through line 24. In the event that the ether is subjected to hydrolysis, the hydrolysis conditions which are employed will include a temperature in the range of from about 150° to about 250° C. and a pressure in the range of from subatmospheric to about 1500 psi. The resulting alcohol and olefinic hydrocarbon are withdrawn from treatment zone 23 through line 25, the alcohol being passed to storage through lines 21 and 25, while the olefinic hydrocarbons may e recycled back to esterification zone 2, by means not shown in the drawing, for use as a portion of the feedstock in this reaction, or utilized as a feed for other processes.

By utilizing the present process, it is possible to operate the same at a maximum efficiency whereby by employing the trans-esterification step of the process utilizing an organic acid with a subsequent hydrolysis employing a stoichiometric amount of water, it is possible to obviate the dilution of the inorganic acid with a concurrent avoidance of the necessity of reconcentrating said acid in order that it may be further utilized as an esterification agent. The elimination of this reconcentration step will greatly reduce the overall expense of the operation and thereby render the same more commercially attractive to operate.

The following examples are given for purposes of illustrating the process of this invention. However, it is to be understood that these examples are given merely for purposes of illustration and that the present process is not necessarily limited thereto.

EXAMPLE I

In this example, 50.8 grams of a 96 wt. % sulfuric acid was placed in a 300 cc stainless steel stirred autoclave. A blend gas consisting of 18.5% ethylene and 81.5% of nitrogen was charged to the reactor until an initial operating pressure of 450 psi was attained. The autoclave was heated to a temperature of 100° C. and stirred at a rate of 560 rpm. The reaction was allowed to proceed for a period of 90 min. at which time heating was discontinued and the autoclave was allowed to return to room temperature. The excess pressure was discharged, the autoclave was opened and an analysis of the reaction mixture determined that there had been a 97% conversion of the ethylene to form a mixture of diethyl sulate and ethyl hydrogen sulfate.

EXAMPLE II

In this example trans-esterification of the alkyl salt was attained by placing 72.2 grams of the diethyl sulfate and 18.5 grams of acetic acid in a 500 cc flask. The flask was heated to a temperature of 91° C. and maintained thereat for a period of 1 hour. At the end of this time, analysis of the reaction mixture disclosed that there had been a 36% conversion of the acetic acid with a 100% mole selectivity to ethyl acetate with a corresponding 99 wt. % recovery. The trans-esterification reaction was repeated by treating the diethyl sulfate with acetic acid at a temperature of 104° C. for a period of 70 min.

There was obtained an 81% conversion of the acetic acid with a corresponding 100 mole % selectivity to ethyl acetate with a 99.5 wt. % recovery. Likewise, when the reaction was effected at a temperature of 120° C. for a period of 60 min., the conversion of acetic acid rose to 97% with a 100 mole % selectivity and a 98.9 wt. % recovery.

EXAMPLE III

To illustrate the separation of a mixture of ethyl acetate, sulfuric acid and reacted diethyl sulfate, a mixture of acetic acid, ethyl acetate, sulfuric acid and diethyl sulfate in a mole ratio of 1:2:0.01:1 respectively was subjected to distillation at a temperature of 110° C. and a pressure of 760 mm of mercury for a period of 45 min. The overhead comprised a mixture of acetic acid and ethyl acetate while the bottoms comprised diethyl sulfate and sulfuric acid. There was obtained a 98.1 mole % recovery of the components of the mixture.

EXAMPLE IV

To illustrate the hydrolysis of ethyl acetate to form ethanol, diethyl ether and acetic acid, a feedstock of water and ethyl acetate was placed in an 850 cc rotating autoclave. The autoclave was heated to a temperature of 150° C. under a pressure of 80 psi and maintained thereat for a period of 2 hours. At the end of this time, heating was discontinued, the excess pressure was discharged and the autoclave was opened. Analysis determined that there had been a 59.4% conversion of the ethyl acetate with a 91.8 wt. % recovery of the product.

EXAMPLE V

The acetic acid which was formed during the hydrolysis of the ethyl acetate may be separated from the ethanol and diethyl ether by subjecting the mixture to a stripping operation utilizing nitrogen as a stripping gas. The stripping of the acetic acid may be effected at a temperature of 90° C. for a period of 0.5 hours. Thereafter, the diethyl ether may be separated from the ethanol in a distillation apparatus by heating the apparatus to a temperature of about 40° C. and recovering the ether. Following this, the diethyl ether may be converted to the desired ethanol by placing the diethyl ether along with water in an autoclave in the presence of a resin such as that sold under the tradename Amberlite XE-365, said conversion being effected at a pressure of about 400 psi and a temperature of about 200° C.

EXAMPLE VI

In a manner similer to that set forth in the above examples, other olefins such as propylene and butylene may be esterified with an inorganic acid such as phosphoric acid followed by trans-esterification with an organic acid such as chloroacetic acid or propionic acid. The resultant organic esters may then be stripped from the reconstituted sulfuric acid and hydrolyzed by treatment with water under operating conditions similar to those hereinbefore set forth. Thereafter, the reconstituted organic acids may be separated from the isopropyl alcohol or sec-butyl alcohol and further utilized in the trans-esterification step while the desired alcohols may be recovered.

I claim as my invention:

1. A process for the hydration of an olefinic hydrocarbon which comprises esterifying said olefinic hydrocarbon with an inorganic acid at esterification conditions in a first esterification zone, subjecting the resultant alkyl salts to trans-esterification by treatment with an organic acid at esterification conditions in a second esterification zone, stripping the resultant organic ester from the reconstituted inorganic acid, hydrolyzing said organic ester with water at hydration conditions in a hydration zone, stripping the resultant alcohol and ether hydrolysis product from the reconstituted organic acid, separating and recovering said alcohol from said ether at separation conditions in a separation zone, treating said ether at treatment conditions in a treatment zone to produce an additional amount of said alcohol, and recovering said alcohol.

2. The process as set forth in claim 1 in which said esterification conditions include a temperature in the range of from about 50° to about 150° C. and a pressure in the range of from about 200 to about 1500 pounds per square inch.

3. The process as set forth in claim 1 in which said stripping of said organic ester and hydrolysis product from said reconstituted acids is effected at a temperaure in the range of from about ambient to about 200° C. and a pressure in the range of from about atmospheric to about 1500 pounds per square inch.

4. The process as set forth in claim 1 in which said hydrolysis conditions include a temperature in the range of from about ambient to about 200° C. and a pressure in the range of from about subatmospheric to about 1500 pounds per square inch.

5. The process as set forth in claim 1 in which said separation conditions include a temperature in the range of from about ambient to about 200° C. and a pressure in the range of from about subatmospheric to about 150 pounds per square inch.

6. The process as set forth in claim 1 in which said treatment conditions include a temperature in the range of from about 150° to about 750° C. and a pressure in the range of from about subatmospheric to about 1500 pounds per square inch.

7. The process as set forth in claim 6 in which said ether is treated by being subjected to decomposition at a temperature in the range of from about 500° to about 750° C. and a pressure in the range of from about subatmospheric to about 1500 pounds per square inch to produce said alcohol and said olefinic hydrocarbon.

8. The process as set forth in claim 6 in which said ether is subjected to hydrolysis at a temperature in the range of from about 150° to about 250° C. and a pressure in the range of from about subatmospheric to about 1500 pounds per square inch to produce said alcohol and said olefinic hydrocarbon.

9. The process as set forth in claim 1 in which said stripping of said organic ester and hydrolysis product from reconstituted acids is effected by treatment with a stripping gas.

10. The process as set forth in claim 9 in which said stripping gas is nitrogen.

11. The process as set forth in claim 1 in which said inorganic acid is sulfuric acid.

12. The process as set forth in claim 1 in which said inorganic acid is phosphoric acid.

13. The process as set forth in claim 1 in which said organic acid is acetic acid.

14. The process as set forth in claim 1 in which said organic acid is chloroacetic acid.

15. The process as set forth in claim 1 in which said organic acid is propionic acid.

16. The process as set forth in claim 1 in which said olefinic hydrocarbon contains from two to about four carbon atoms.

17. The process as set forth in claim 16 in which said olefinic hydrocarbon is ethylene, said alcohol is ethyl alcohol, and said ether is diethyl ether.

18. The process as set forth in claim 16 in which said olefinic hydrocarbon is propylene, said alcohol is isopropyl alcohol, and said ether is diisopropyl ether.

19. The process as set forth in claim 16 in which said olefinic hydrocarbon is butylene, said alcohol is sec-butyl alcohol, and said ether is di-sec-butyl ether.

* * * * *